(12) United States Patent
Landis

(10) Patent No.: US 6,559,771 B2
(45) Date of Patent: May 6, 2003

(54) SENSING AND MEASURING CIRCUIT EMPLOYING A POSITIVE-TEMPERATURE-COEFFICIENT SENSING DEVICE

(75) Inventor: Donald G. Landis, deceased, late of Hollis, NH (US), Sally A. Landis, administratrix

(73) Assignee: Lansense, LLC, Hollis, NH (US)

(*) Notice: Subject to any disclaimer, the term of this patent is extended or adjusted under 35 U.S.C. 154(b) by 48 days.

(21) Appl. No.: 09/949,687

(22) Filed: Sep. 12, 2001

(65) Prior Publication Data

US 2003/0048189 A1 Mar. 13, 2003

(51) Int. Cl.[7] .............................................. G08B 21/00
(52) U.S. Cl. ..................... 340/603; 340/604; 340/618; 340/622; 73/73; 73/75; 338/22 R; 338/13
(58) Field of Search ................................ 340/603, 604, 340/618, 622; 73/73, 75; 338/22 R, 13

(56) References Cited

U.S. PATENT DOCUMENTS

| | | | | |
|---|---|---|---|---|
| 4,031,499 A | | 6/1977 | Brueckner ................. 338/23 |
| 4,647,919 A | * | 3/1987 | Wright et al. ............... 340/608 |
| 4,656,464 A | * | 4/1987 | Cliffgard .................... 340/622 |
| 4,890,494 A | | 1/1990 | Osbond et al. .............. 73/338 |
| 5,339,689 A | * | 8/1994 | Hegge ........................ 73/295 |
| 5,369,396 A | * | 11/1994 | Kurata et al. ............... 340/623 |
| 5,402,111 A | | 3/1995 | Hubbard, Jr. ............... 340/608 |
| 5,805,393 A | * | 9/1998 | Thomas ....................... 361/6 |
| 6,373,347 B1 | * | 4/2002 | Cogan .......................... 333/81 |
| 6,411,192 B1 | * | 6/2002 | Landis .......................... 338/25 |

OTHER PUBLICATIONS

Supplemental Catalog—Keystone Thermometrics Corp. St. Mary's, Pennsylvania 1996, pp. 31 through 38.

* cited by examiner

Primary Examiner—Julie Lieu
(74) Attorney, Agent, or Firm—Robert G. Crooks

(57) ABSTRACT

A sensing and measuring circuit, employing a positive-temperature-coefficient sensing device, for detecting the presence and approximately measuring the quantity or concentration of heat-absorptive substances such as water. May be used for sensing a quantity of rainfall or irrigation water, or for detecting and giving an alarm or initiating remediation for leakage of water, oil, or other fluids from confinement to an unauthorized location.

23 Claims, 10 Drawing Sheets

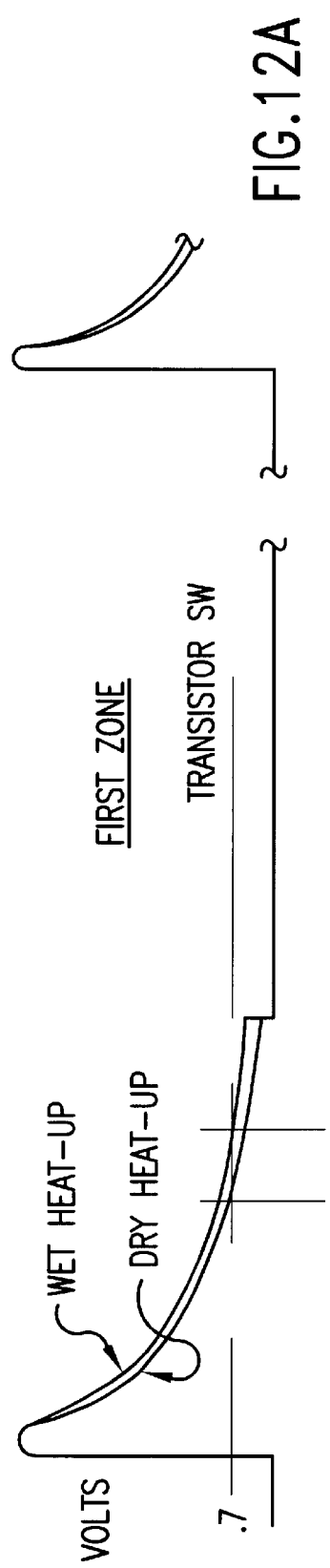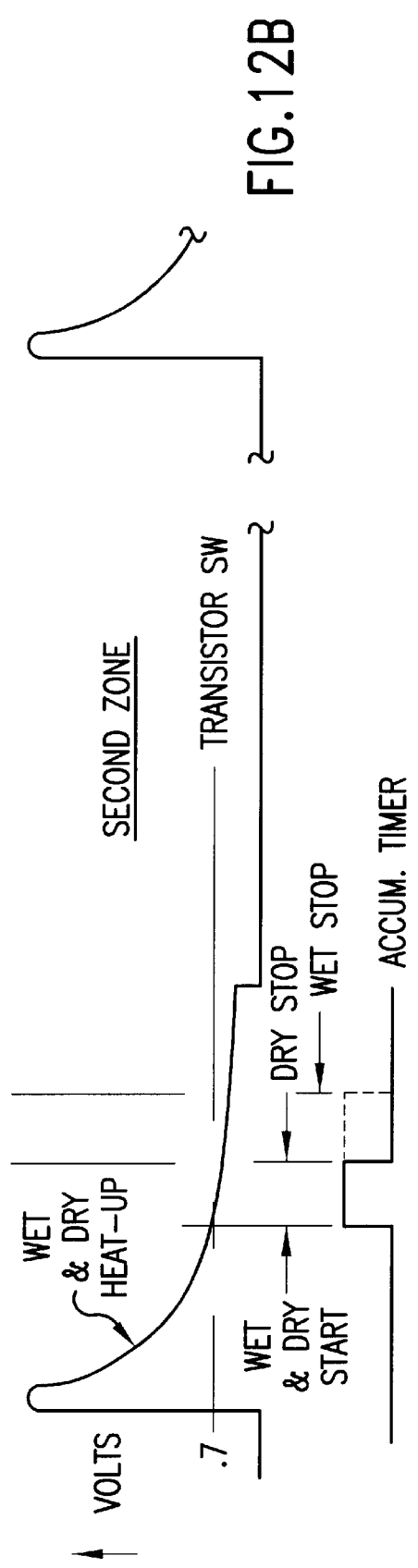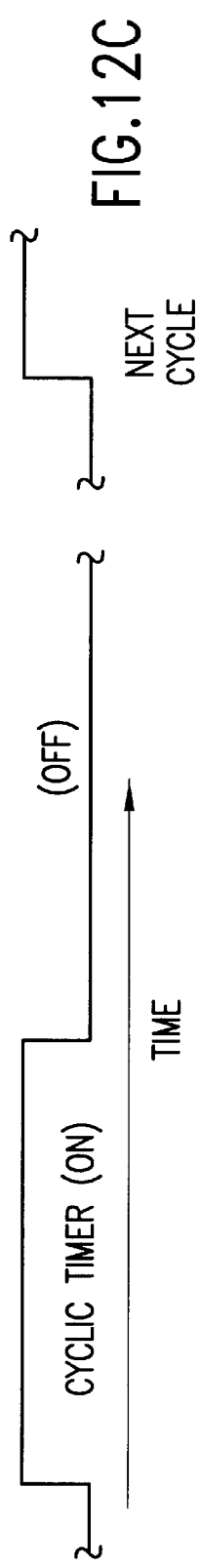

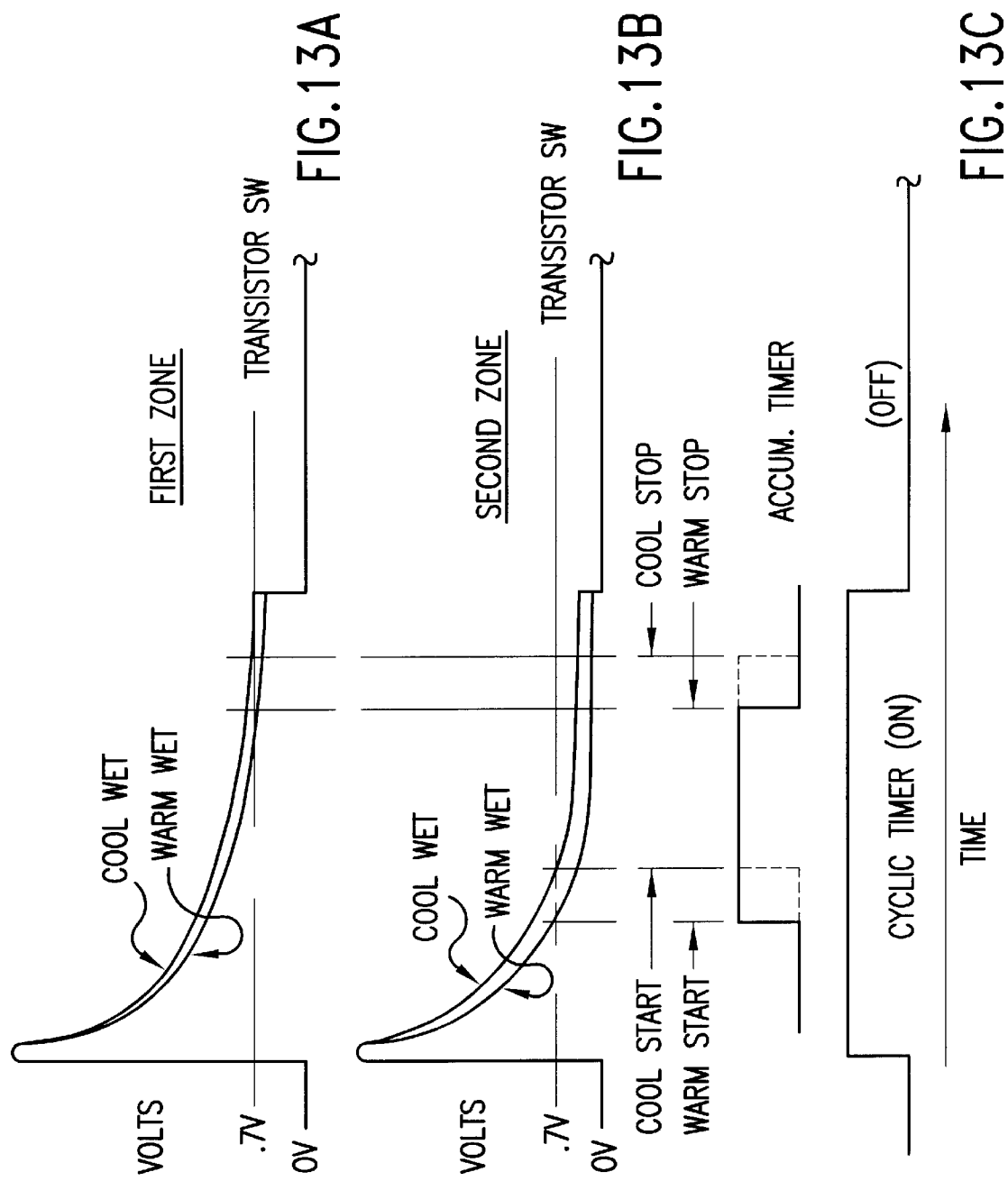

SENSING AND MEASURING CIRCUIT EMPLOYING A POSITIVE-TEMPERATURE-COEFFICIENT SENSING DEVICE

BACKGROUND OF THE INVENTION

1. Field of the Invention

This invention relates to a sensor and associated circuitry for sensing and measuring the presence of a fluid, permeable medium, fluid carried by a solid medium, or other substance, and to a method for using the sensor and associated circuitry. It also relates to an apparatus and method for performing a switching step when the amount of the fluid, the amount of the permeable medium, or the concentration of the fluid carried by said medium reaches a certain level.

Typical applications of the invention are as follows:
(a) Detecting a quantity of rainfall or dispensed water upon an area of land served by an irrigation system;
(b) Sensing leakage, spillage or overflow of oil within a wall surrounding an oil-storage tank;
(c) Detecting leakage of liquid from a conduit into insulation or another substance; and
(d) Making an approximate appraisal of moisture suspended within a sample of earth.

When a quantity of rainfall, the spillage of oil, or the suspension of moisture in a medium is detected, appropriate circuitry produces an electrical signal to operate an alarm or suitable control equipment as required by the circumstances.

Preferably, the sensor comprises at least one positive-temperature-coefficient ("PTC") device coupled to single or plural signal-processing circuits or sub-assemblies for actuating any desired output apparatus for indication or control.

2. Description of the Prior Art

Attention is invited to my co pending application Ser. No. 09/221,733, filed on Dec. 28, 1998 and entitled "Method and Apparatus for Sensing and Measuring Plural Physical Properties, Including Temperature." That application discloses and claims an arrangement including at least one "tablet" of positive-temperature-coefficient ("PTC") material with a plurality of zones that have some electrical and thermal dependence upon each other. The arrangement permits the measurement of at least one physical property, including temperature.

Typically, PTC material comprises a mixture of barium and/or strontium titanates suitably "doped" with certain trivalent or pentavalent elements that serve to adjust the temperature at which the material reaches its "Curie point." At about the Curie point, a plot of resistance of the material as a function of its temperature becomes very steep as temperature increases further. At still higher temperatures, the plot levels off at a "knee" as shown in FIG. 1 of the drawings of that application and of this specification. The characteristics of PTC materials are well described in a publication of Keystone Thermometrics, of St. Mary's, Pa., a copy of which is made a part of the file of this specification.

An "Atmospheric Sensor" employing PTC material is shown and described in U.S. Pat. No. 4,890,494—Osbond et al, which is also entered in the file of this specification. That patent discloses a probe of PTC material for measuring the liquid content of a gas. But Osbond et al do not reveal a sensor, which may comprise a single tablet of PTC material divided into zones, which are nevertheless electrically and thermally dependent upon each other. Nor do Osbond et al disclose a circuit having a time-dependent thermal-resistive response to the initialization of an electric potential.

SUMMARY OF THE INVENTION

In view of the distinctions of the present invention over the prior art, I have provided a sensing and measuring circuit that is new in its concept and surprising in its capabilities, while employing a modest amount of hardware.

The sensing circuit in accordance with the present invention is built around a tablet of PTC material to which are bonded, preferably on a first side and a second side thereof respectively, first and second respective layers of ohmic resistive (or conductive) material. While the first such layer is continuous in configuration, the second layer is separated into a first zone and a second zone, which are not in direct electrically-conductive relationship with each other. The first layer is connectable, through switching or other means, to a first source of electric potential "+V." The second zone of the second layer is grounded, or connected to a second source of different electric potential.

The first zone of the second layer is in physical contact with a body which, from its standpoint, is a heat sink. The body may, for instance, comprise a diaphragm on the opposite side of which may be present (or not be present) drops of water or other fluid. The first zone of the second layer may be electrically connected through first and second series-resistor means to ground or a source of different electric potential.

The junction or node between the first and second series-resistor means is coupled to the input of a switching device such as an NPN transistor. The output terminals of the switching device may be connected through a gating device to an alarm, a signal light, a control valve, a motor switch, a meter, or other output device.

Means may be provided for periodically applying the voltage "+V" to the first layer of ohmic material. When voltage "+V" is first applied to the first layer, the temperature of the tablet of the PTC material is low, and the current through it immediately becomes high. But, as the current warms the tablet, portions of it reach the Curie point and sharply increase in resistance. Accordingly, the current flowing through the second zone of the second layer and the portion of the tablet of PTC material proximate thereto will sharply decrease.

The portion of the tablet of PTC material which is in contact with the heat sink and with the first zone of the second layer of ohmic resistive material will warm up more slowly than the portion of the tablet proximate the second zone of the second layer. And if the heat sink includes a diaphragm carrying drops of water, oil, or other liquid of high heat capacity, the portion of the tablet proximate the first zone of the second layer will warm up still more slowly. The warm-up time as seen through the first zone of the second layer, when compared with the warm-up time as seen through the second zone of the second layer, will be substantially greater. Moreover, the time disparity will increase with the concentration of heat-absorbing water or oil or other material (the "heat sink") on the opposite side of the diaphragm or other structure that is in physical contact with the portion of the tablet of PTC material proximate the first zone of the second layer of ohmic resistive material.

The time disparity may be sensed by means of a comparator having one input terminal connected to the first zone of the second layer of ohmic material while the other input terminal is connected to the second zone of the said second layer. For each sensor and for each type of material comprising the "heat sink", one may compile a correlation table relating the time disparity to the amount or concentration of material in the heat sink.

Without more, such a correlation table would be accurate only for given bands of operating temperatures of the two portion's of the PTC material. However, a high degree of temperature compensation may be achieved to insure accuracy and reliability of operation over a considerable range of ambient temperatures of the medium in which the tablet of PTC material is accommodated. This temperature compensation may be realized by loosely coupling to the heat sink the portion of the tablet proximate the second zone of the second layer of ohmic material while maintaining tight thermal coupling between the heat sink and the portion of the tablet proximate the first zone of the second layer. To this end, the tablet and its ohmic layers may be supported by a foam having some thermal conductivity, while the assembly of tablet, ohmic layers and foam is confined within a cup or other structure which isolates the assembly from rapid changes in ambient temperature.

BRIEF DESCRIPTION OF THE DRAWINGS

The invention summarized above will be described in detail in the following specification, which will be best understood if it is read while referring to the accompanying drawings, in which:

FIG. 12A is a second plot of respective voltages across resistor means between ground and the first zone of the second ohmic layer of the sensor when moisture is present on the surface of the diaphragm and, again, when moisture is not present;

FIG. 12B is a plot of voltage across resistor means between ground and the second zone of the second ohmic layer of the sensor when moisture is and is not present on the diaphragm;

FIG. 12C is a plot, correlated in time to the respective plots of FIG. 12A and FIG. 12B, indicating the reading of the accumulation timer, and another plot, once again correlated in time to the aforementioned plots, indicating the gating action of a cyclic timer controlling the energization of the first ohmic layer of the sensor by a source of positive voltage, all while assuming that the ambient temperature around the sensor remains constant;

FIG. 13A is a third plot of respective voltages across resistor means between ground and the first zone of the second ohmic layer of the sensor when moisture is present on the surface of the diaphragm, first when the ambient temperature (and that of the moisture) is warm and, second, when the ambient temperature is cool, but without changing the moisture level;

FIG. 13B is a plot of respective voltages across resistor means between ground and the second zone of the second ohmic layer of the sensor for warm and cool ambient temperatures while, again, the moisture level remains constant;

FIG. 13C is a plot, correlated in time to the respective plots of FIG. 13A and FIG. 13B, indicating the reading of the accumulation timer, and another plot, once again correlated in time to the aforementioned plots, indicating the gating action of the cyclic timer controlling the energization of the first ohmic layer of the sensor by a source of positive voltage, all while assuming that the moisture level remains constant;

DETAILED DESCRIPTION OF THE PREFERRED MODE OF CARRYING OUT THIS INVENTION

Figure 1:
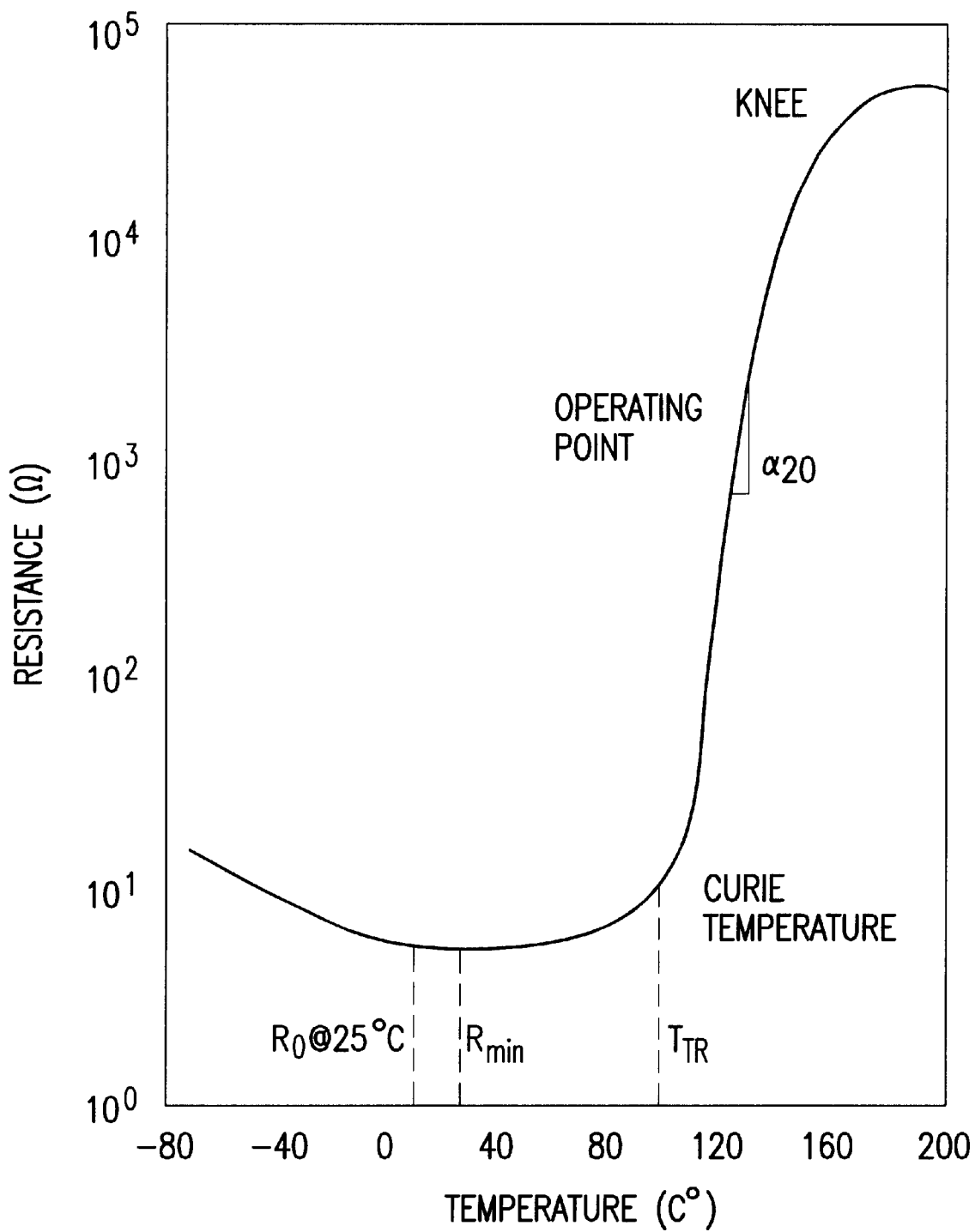
FIG. 1 is a plot of a typical relationship of electrical resistance of a PTC material as a function of its temperature, both above and below the "Curie" transition temperature.

Referring first to FIG. 1 of the drawings, we see a plot of electrical resistance, shown on a logarithmic scale, of a positive-temperature-coefficient ("PTC") material per se, as marketed commercially by the Keystone Thermometrics Company of St. Mary's, Pa., among others. The plot shows how, as temperature increases, the resistance of the material dips slightly to a minimum value and then rather suddenly increases at the transition temperature commonly known as the "Curie Point." And the resistance then continues to increase at a very sharp rate with respect to the corresponding increase in temperature, at least up to a rather ill-defined "knee" of the curve, where it begins to level out. Within a certain narrow temperature range, the slope of the curve of resistance as a function of temperature is so steep that one is tempted to regard it as vertical. Of course, it is not truly vertical, but nevertheless a very small change in temperature produces a very large change in resistance, which is not fully dramatized by the logarithmic scale of FIG. 1.

The PTC material is likely to be primarily barium titanate, admixed with certain other titanates and compounds which can "adjust" the position of the "Curie temperature" from below the freezing point to well above the boiling point of water. Specifications of various PTC materials are available from Keystone and others.

Figure 2:
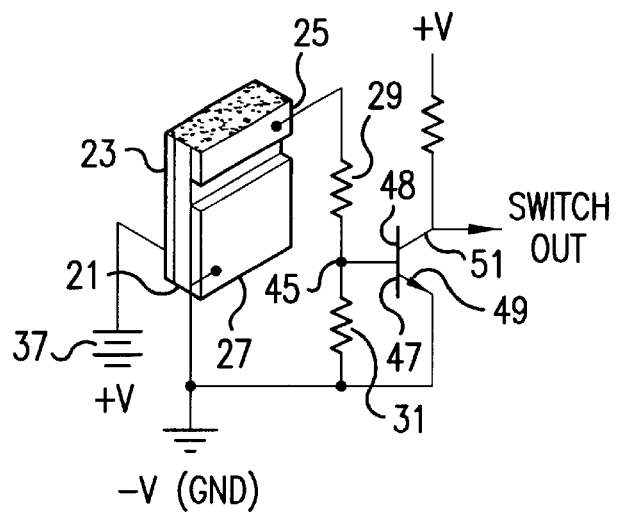
FIG. 2 is a schematic representation, partly in perspective, of the electrically-functional elements of a sensor and simple switch in accordance with this invention.

Turning to FIG. 2 of the drawings, we see the electrical circuitry of a sensor and simple switch in accordance with this invention. A principal element of the sensor is a tablet 21 of PTC material, shown roughly in the configuration of a parallelepiped, which may be rounded on the top end.

PTC material is available from Keystone and others in various physical forms. Commonly, tablets of PTC material are sold in the form of a rectangular prism. Alternatively, they can be purchased in circular-cylindrical form, like "pills". In either case, the titanate composition is likely to be covered on two flat sides by respective layers of material having an ohmic characteristic so as to spread an applied electric potential evenly over the side surfaces of the semi-conductive PTC material. The layers of ohmic material are bonded to respective side surfaces of the tablet or pill of PTC material.

In the configuration of FIG. 2, a first layer 23 of ohmic material is bonded to a first side of tablet 21, while the second side of tablet 21 is covered, in bonded fashion, by a first zone 25 and a second zone 27 of ohmic material which are distinct from one another. The distinctness may be achieved by removing a narrow channel of the ohmic material from the continuous covering bonded to the second side of the tablet by the manufacturer.

First zone 25 is connected through a first series resistor 29 and a second series resistor 31 to ground, or to a source of preferably negative potential. Second zone 27 is connected to ground or said source of negative potential. Series resistors 29 and 31 constitute a voltage divider.

Figure 5:
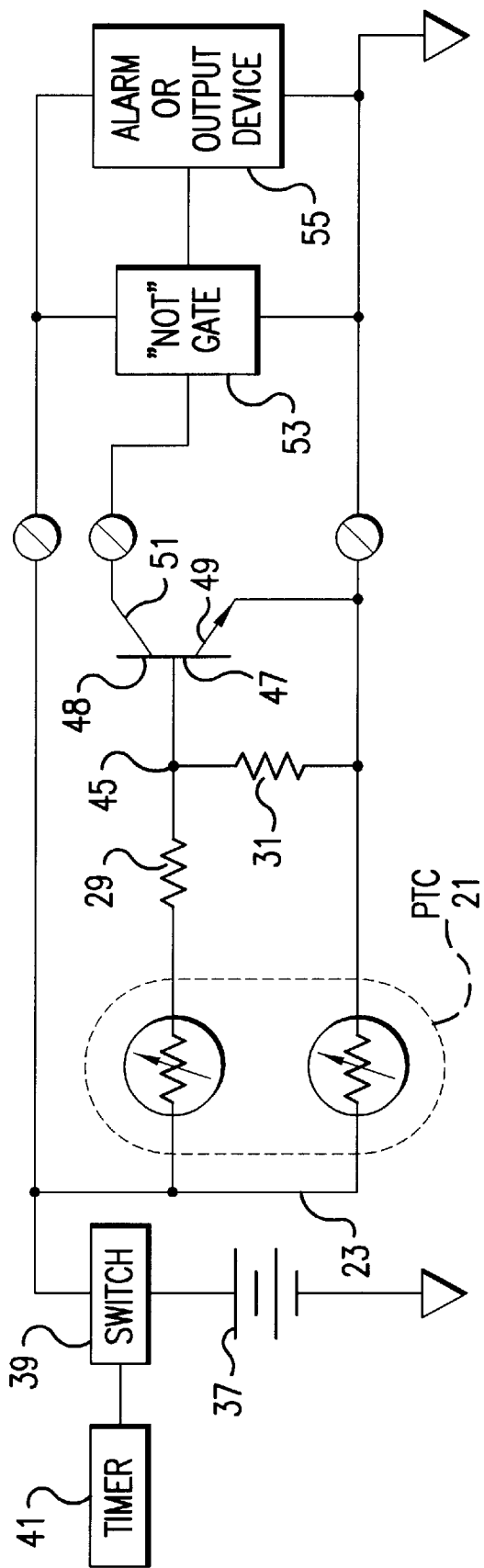
FIG. 5 is a schematic representation of simple but complete electronics for a sensing and switching circuit in accordance with this invention, without showing the heat sink, and in which the tablet of PTC material has been represented as a parallel combination of two variable resistances.
Figure 10:
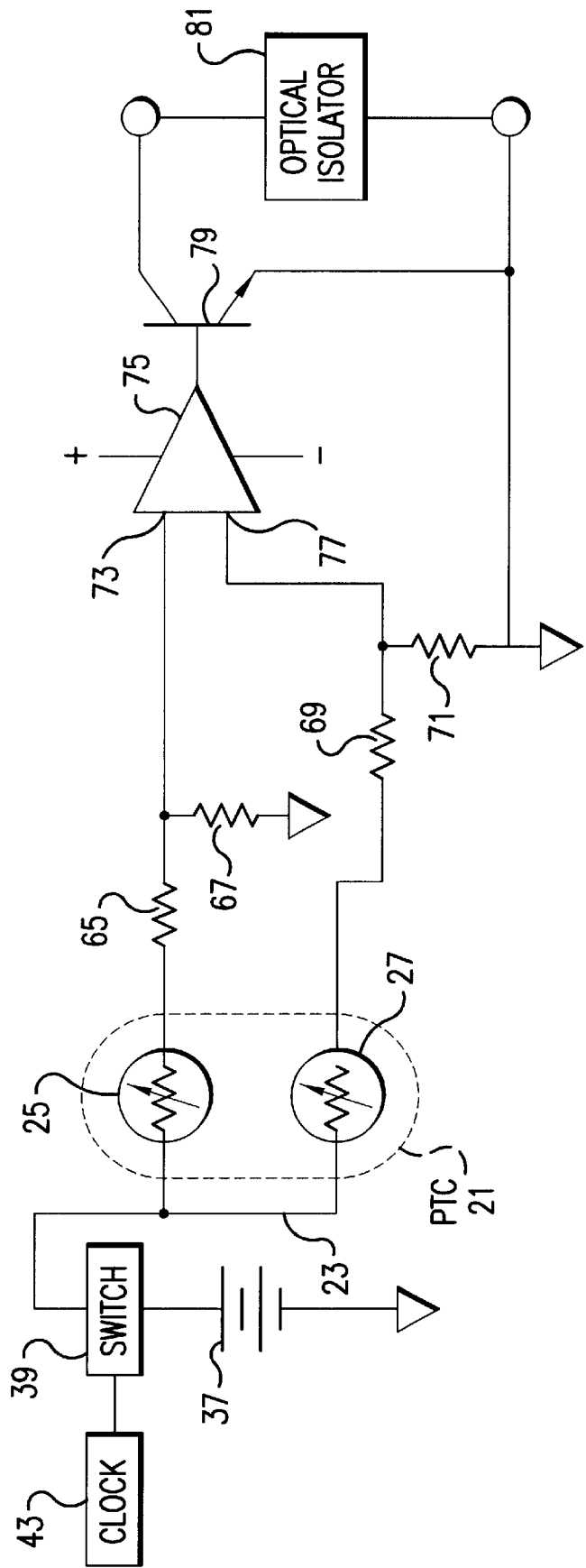
FIG. 10 is a schematic representation of a sensing and measuring circuit in accordance with this invention in which a comparator receives respective signals from the first and second zones of the second ohmic layer of the sensor in order to provide compensation of output during fluctuations of ambient temperature as a function of time.

The portion of tablet 21 proximate first zone 25 of ohmic material may be placed in physical contact with any substance characterized by significant heat capacity, or specific heat. Such physical contact may be direct or through an intervening membrane such as the diaphragm 33 shown in FIG. 3 and FIG. 4 of the drawings. One of the objects of the invention is to sense the presence of a substance having heat capacity and located on the side of the membrane or diaphragm remote from tablet 21;

For the purpose of explanation, let us assume the presence of water drops 35 on top of diaphragm 33. Now, if first layer 23 is connected to a source 37 of positive potential, a first electric current will flow through first layer 23, tablet 21, first zone 25, first series resistor 29, and second series resistor 31 to ground. A second electric current will flow through first layer 23, tablet 21, and second zone 27 to ground. Both currents may be initiated, if desired, by the closure of a switch 39 as shown in FIG. 5 and FIG. 10, the operation of which may be controlled by a timer 41 as shown in FIG. 5 or a clock 43 as shown in FIG. 10.

When the voltage "+V" of source 37 is applied to first layer 23, tablet 21 is at ambient temperature. At that temperature, the resistance of tablet 21 is near its minimum value, as shown by the plot of FIG. 1. Tablet 21 is below its Curie temperature. Stated conversely, a PTC material will have been chosen for tablet 21 such that the Curie temperature of the material is appreciably higher than the temperature of the environment in which the sensor and switch of this invention are expected to be operated. As has been explained, the manufacturer can supply PTC material which has been blended to have a Curie temperature somewhat higher than most comfortable environments. Referring again to FIG. 1, the Curie temperature of approximately 95 degrees Centigrade is appreciably higher than room temperature of about 20 degrees Centigrade.

If the sensor and switch are to operate rapidly, source 37 may have a voltage "+V" of approximately 24 volts. Typically, the "cold" resistance of tablet 21 is in the vicinity of 50 ohms. Accordingly, a total current of several hundred milliamperes can be expected to flow through tablet 21. But from the time of the first surge after closure of switch 39, the current density is non-uniform through the cross section of tablet 21 and it becomes moreso as time passes. To a first approximation, the total current can be considered as the sum of the first current, through first zone 25, and the second current, through second zone 27.

The "$I^2R$" heating produced by the second current flowing through the end of tablet 21 proximate second zone 27 and most remote from first zone 25 causes that end of tablet 21 to warm up rapidly and soon reach its Curie temperature, whereupon its resistivity increases sharply. On the other hand, the "$I^2R$" heating produced by the first current flowing through the end of tablet 21 proximate first zone 25 produces warming more slowly; consequently, that end of tablet 21 reaches its Curie temperature somewhat later. This delay is attributable to the heat flow from that end of tablet 21 through diaphragm 33 and into water drops 35. Even if the water drops were not present, the end of the tablet 21 proximate first zone 25 would probably warm up slightly more slowly than the end proximate second zone 27 because of the finite heat loss into diaphragm 33, however small.

So, the two ends of tablet 21 will attain the Curie temperature and increase sharply in resistance at different instants. In each case, the current flowing through that end of tablet 21 will decrease. The second current is determined primarily by the voltage "+V" from source 37 and by the resistivity of second zone 27 and that of the portion of tablet 21 proximate second zone 27. The second current will decrease rapidly until its portion of tablet 21 finds a stable operating point on the plot of resistance versus temperature as shown in FIG. 1. The operating point may be at the place indicated on the steep slope of that plot.

The first current, on the other hand, is determined by first series resistor 29 and second series resistor 31 as well as voltage "+V" and the resistance of first zone 25 and that of the portion of tablet 21 proximate first zone 25. As has been noted, the latter resistance is slower to increase than that of second zone 27, and must be analyzed together with series resistors 29 and 31, whose purpose will now be explained.

The first node 45 between first series resistor 29 and second series resistor 31 may be connected to the base 47 of a first transistor 48 having also an emitter 49 and a collector 51. For the purpose of discussion, let us assume that the transistor is an NPN device, and that emitter 49 is grounded, as are second zone 27 and the end of second series resistor 31 remote from first node 45. Then, if the voltage on base 47 is less than 0.7 or is negative, there will be no current between emitter 49 and collector 51. However, the magnitude of second series resistor 31, relative to the sum of the resistances of first series resistor 29 and cold tablet 21, is chosen so that more than 0.7 volt will appear across it when switch 39 is closed and current rushes through tablet 21 in its low-resistance state. Thus, after closure of switch 39, the transistor immediately turns on. But that turn-on and the indication thereof may not be useful information other than to confirm the closure of switch 39. As will be made clear in following paragraphs, the more significant transition may take place when the transistor turns off.

While serving as a voltage divider determining the bias voltage on the transistor, first series resistor 29 and second series resistor 31 must also be selected to permit sufficient current to flow through first zone 25 to allow the portion of tablet 21 proximate first zone 25 to reach the Curie temperature, albeit not as rapidly as does the portion of tablet 21 proximate second zone 27. The sensitivity and response time of the sensor and switch are partially determined by choice of resistance values. And those resistance values derive their significance from the resistance of tablet 21, both below and above the Curie temperature.

Figure 3:
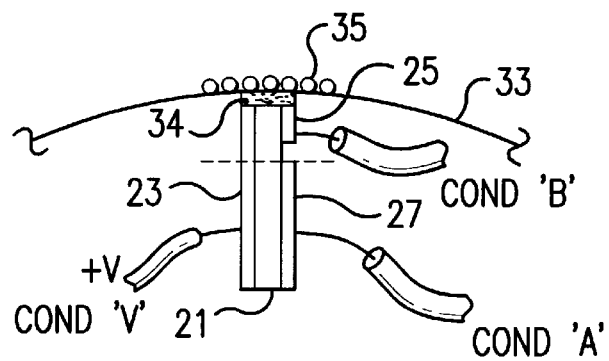
FIG. 3 is a side view, partly in section, of a sensor in accordance with this invention in which the portion of the tablet of PTC material proximate the first zone of the second layer of ohmic material is also in physical contact with a thin diaphragm in the form of a shallow dome.
Figure 4:
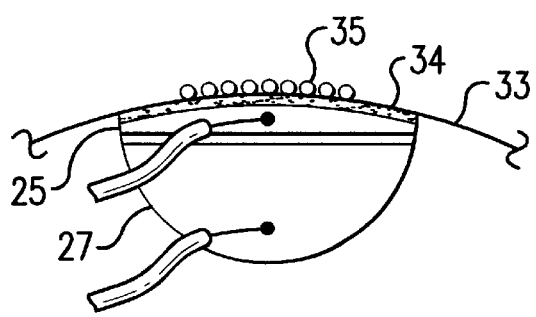
FIG. 4 is a front view, again partly in section, of the sensor shown in FIG. 3, similarly in contact with a shallow-dome diaphragm, and showing clearly the cut in the surface of the second layer of ohmic material that separates the first zone thereof from the second zone.

In order to discuss resistances of the sensor and circuitry in a commercially useful form, let us turn to FIG. 3 and FIG. 4 of the drawings. Those figures show, respectively in side view and front view, a tablet 21 in the configuration of a half cylinder. The half cylinder has been formed by dividing a cylinder of PTC material by a diametrical plane passing through the axis of the cylinder, and then by buffing the cut surface of one half cylinder to allow it to interface closely with diaphragm 33 in the form of a shallow dome. One suitable barium titanate product of Keystone has a diameter of 0.31 inch and an axial thickness of 0.4 inch. The channel cut through the second layer of ohmic material to separate first zone 25 from second zone 27 is shown in both figures, but is especially apparent in FIG. 4. The tablet may be adhered to diaphragm 33 by a thin layer of thermal epoxy 34.

Now, with reference to FIG. 2 and the schematic representation of FIG. 5, some numerical values of typical components and currents will be given. It should be remembered that the numerical values to be presented are exemplary only, and should not be interpreted in a limiting sense. It should also be borne in mind that the components and currents should be such as to allow the entire bulk of tablet 21 to reach the Curie temperature, but that the portion of tablet 21 proximate first zone 25 will be slower in attaining that temperature than the portion proximate second zone 27 if there is a significant amount of heat-capacity material in contact with diaphragm 33 or with the portion of tablet 21 proximate zone 25.

After the closure of switch 39 and the initiation of current flow through tablet 21, the tablet begins to dissipate heat to its environment. If the environment is simply air, as is the case with the portion proximate second zone 27, the rate of heat dissipation is relatively low. But if drops of water or other heat-capacity material are present on the diaphragm, the rate of heat dissipation from the portion proximate first zone 25 will be somewhat higher. Consequently, the rate of build-up of temperature in that portion of tablet 21 will be lower, the Curie temperature will be attained later, and the attenuation of current through first zone 25, first series resistor 29, and second series resistor 31 will be somewhat delayed. Accordingly, the turn-off of the transistor is likewise delayed, as clearly illustrated in FIG. 9A and FIG. 9B. The length of the delay is a measure of the amount of water, or other heat-capacity substance, which is present on the surface of diaphragm 33. The amount of delay produced by the heat capacity of the diaphragm itself is either negligible or can be taken into account in the calibration of the sensor and switch. Let us next consider an illustrative example, including representative numbers which, again, are not to be taken in a limiting sense:

In order to allow the portion of tablet 21 proximate first zone 25 to heat up rapidly after switch 39 is closed, the series combination of first series resistor 29 and second series resistor 31 is preferably set at a low level such as 50 ohms. A typical minimum value for the resistance of a tablet of PTC material is also 50 ohms. As shown by the plot of FIG. 1, the minimum resistance of a tablet of PTC material may be even less than 50 ohms. The state of minimum resistance occurs when the PTC material is warming up to the Curie temperature (or cooling off from it). Again, assuming that the direct voltage "+V" is 24 volts, the initial current through series resistors 29 and 31 may be of the order of 0.24 ampere. Consequently, unless the value of second series resistor 31 is very small compared with the value of first series resistor 29, the voltage developed across second series resistor 31 will be well in excess of the 0.7 volt on base 47 which is required in order for the transistor to be in a conductive state between emitter 49 and collector 51. Accordingly, since that condition signifies only the closing of switch 39 and the warm-up of tablet 21, it may be desired to indicate the absence of a meaningful signal by including in the circuit a "NOT gate" 53 as shown in FIG. 5 of the drawings. Thus, the turn-on of the transistor would not actuate an alarm 55 or other output device coupled to NOT gate 53 as also shown in FIG. 5.

When tablet 21 reaches the Curie temperature, its resistance increases sharply and should attain levels between 800 and 1000 ohms. But, because of the self-stabilizing nature of PTC material, the resistance will reach a quiescent operating point if nothing else in the circuit changes in value. It is desirable to select the rating of the tablet such that the quiescent operating point will be high on the steep portion of the plot of FIG. 1 but not so high as the "knee". Both portions of tablet 21 will then be in a "steady state" as long as the rate of heat dissipation by both portions remains constant. Meanwhile, the current through the portion of tablet 21 proximate first zone 25 will have fallen from the order of 0.24 ampere to a level ten or twenty percent of that "quiescent" level.

When the resistance of the portion of tablet 21 proximate first zone 25 increases and the current through first series resistor 29 and second series resistor 31 decreases sharply, then the relative values of those resistors become important. Inasmuch as the series resistors form a voltage divider from which the current of base 47 of the transistor is drawn, the conductive state of the transistor depends upon the ratio between the values of those resistors.

Not only does the conductive state of the transistor depend upon the ratio between the respective values of the series resistors but it also depends upon the rate of heat dissipation from the portion of tablet 21 proximate first zone 25. If the rate of heat dissipation (to water or other heat-capacity material in contact with diaphragm 33) increases, the temperature of that portion of tablet 21 decreases. And the resistance of that portion decreases at a rate determined by the steep slope of the plot of FIG. 1. If the presence of such heat-capacity material is to be detected and indicated, then the values of the series resistors, which help to determine the bias of the transistor, become important. Let us consider a specific example of an operating sensor and switch, giving typical values of components, currents, voltages and rates of heat transfer. Again, these values are not to be treated in a limiting sense.

Let us assume, once again, that the total resistance of the series resistors 29 and 31 is 50 ohms. That total must be apportioned between the two resistors such that, when the resistance of the portion of tablet 21 proximate first zone 25 stabilizes at its quiescent operating point without the presence of heat-capacity material, the transistor will be turned off. If the value of first series resistor 29 is set at 33 ohms while the value of second series resistor 31 is set at 17 ohms, a current of 0.03 ampere (12.5% of the "quiescent" level) will flow. Then a voltage of 0.51 volt will appear across second series resistor 31 and also between base 47 and emitter 49 of the transistor. Under those circumstances, the transistor will indeed be turned off.

I have found that a desirable quiescent operating resistance on the steep portion of the plot of FIG. 1 is between 800 and 850 ohms for the portion of tablet 21 proximate first zone 25. Thus, a current of 0.03 ampere would dissipate ($I^2R$) heat at the rate of about 0.75 watt in the portion of tablet 21 proximate first zone 25.

If even a small amount of water, for instance, is suddenly present on the surface of the diaphragm, the initial rate of total heat dissipation and transfer from that portion to the water increases to approximately 1.2 watts. Assuming that about ninety percent of the twenty-four volts derived from source 37 appears across the portion proximate first zone 25, that power implies a current flow which has increased from 0.03 ampere to 0.055 ampere. ((1.2/(24×0.9)). A current flow of 0.055 ampere through first series resistor 29 and second series resistor 31 would develop a voltage of 2.75 volts. Of that amount, 0.93 volt would appear across second series resistor 31, and also between base 47 and emitter 49 of the transistor. The current thus made available to base 47 would be more than adequate to cause the transistor to switch on again.

It will be understood that the aforementioned resistance values are not the only ones which may be employed in the practice of this invention. If the sensor of the invention is to be employed with a switch to indicate the appearance of heat-capacity material (such as water) on the surface of diaphragm 33, the sum of the series resistors should have a total value somewhere between one-fifth and one-twentieth the amount of the quiescent resistance of the portion of tablet 21. For instance, in the above illustration, 50 ohms, the total of the series resistors, is abut 0.06, the value of the assumed quiescent resistance, which is 20% more than one-twentieth, and much less than one-fifth.

In the illustration just presented, the main emphasis was on detecting and indicating the appearance of any substantial amount of heat-capacity material on the surface of diaphragm 33.

On the other hand, if the emphasis is on making a rough appraisal of the amount or concentration of such heat-capacity material, that can be done by adjusting the relative values of first series resistor 29 and second series resistor 31, thereby varying the length of time which elapses between closure of switch 39 and the instant when the transistor turns off.

Figure 9A:
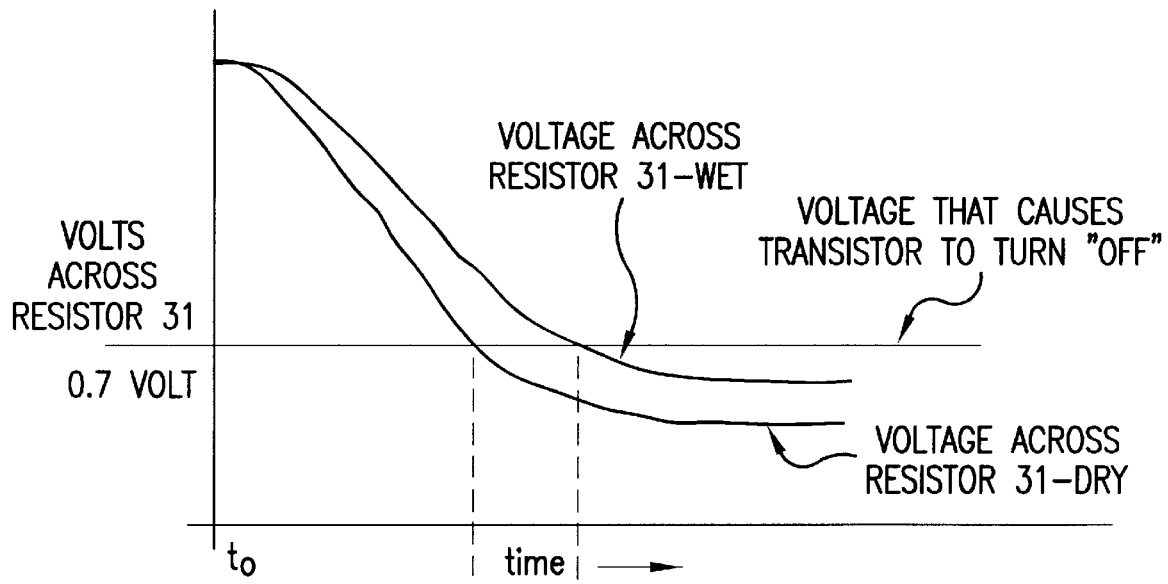
FIG. 9A is a first plot of the respective voltages across series-resistor means between ground and the first zone of the second ohmic layer of the sensor when moisture is present on the surface of the diaphragm and, again, when moisture is not present.

It has been explained that, in one application of this invention, the steady-state condition of the transistor is "off" if no heat-capacity material is present on the surface of diaphragm 33. But, upon the sudden appearance of heat-capacity material on the diaphragm, the current through the series resistors causes the transistor quickly to turn "on". Now, if we are willing to adjust the relative values of the series resistors so that the steady state of the transistor is off even when heat-capacity material is present on diaphragm 33, another new and useful application of the invention becomes possible, as follows:

This time, let us set first series resistor 29 at 40 ohms, while second series resistor 31 becomes 10 ohms. Thus the total series resistance remains the same, but the ratio between the two resistances is changed to decrease the forward bias of the transistor. The transistor still conducts for a brief period of time after the closure of switch 39 and before the portion of tablet 21 proximate first zone 25 reaches the Curie temperature. But, as that portion attains the Curie temperature and sharply increases in resistance, the current flowing therethrough and through the series resistors decreases so that the voltage across second series resistor 31 falls off as shown in FIG. 9A. When that voltage falls through a level of approximately 0.7 volts, the transistor turns off.

It is contemplated that the sensing and measuring circuit in accordance with this invention may be operated on a cyclical basis by periodically closing switch 39, taking a reading or observation after the steady state has been reached, and then opening the switch. Before re-closing switch 39, sufficient time should be allowed for tablet 21 to cool back down to ambient temperature. This "cooling-off period" might be ten or twenty minutes if no artificial cooling is employed. Although a new cycle might be initiated at that time, a clock 43 (FIG. 10) may instead be set to "take another sample" every hour, or every four hours, or every twenty-four hours, whatever cycling period suits the purpose of the operator. However, the operating conditions should be replicated as nearly as possible from cycle to cycle except for the presence or absence of heat-capacity material on the surface of diaphragm 33. In that way, a meaningful comparison may be made between the time to transistor cut-off in one cycle and the time to transistor cut-off in the next, or another, cycle.

Figure 9B:
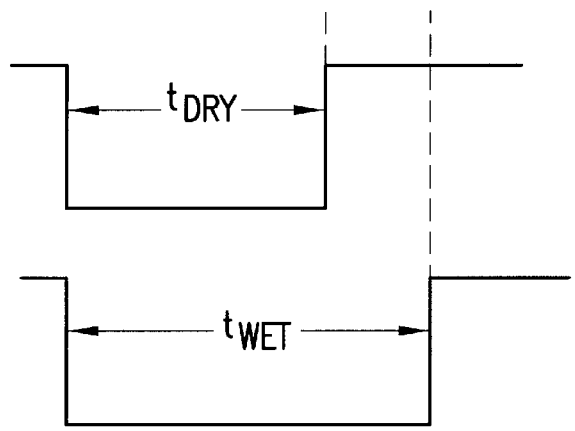
FIG. 9B is a plot, correlated in time to the plot of FIG. 9A, showing current through the collector and emitter of a transistor to the base of which is fed current drawn from a selected portion of the aforementioned series-resistor means, depending upon whether moisture is or is not present on the surface of the diaphragm.

The comparison between respective cut-off times is illustrated in FIG. 9B. In the captions of that figure, the tacit assumption has been made that the heat-capacity material is water. But it could be earth containing suspended water, or it could be oil that has overflowed from a storage tank. By comparing the time to transistor cut-off with a "dry" diaphragm with any other cut-off time which is significantly longer, valuable information about the presence of a heat-capacity material is obtained. And, with the help of a calibration curve, the difference in cut-off times gives a measure of the amount of heat-capacity material. It could also give a measure of rate of flow of heat-capacity liquid along the surface of diaphragm 33. A typical application of this mode of the invention is to shut off an irrigation system when the water content in irrigated earth in contact with diaphragm 33 reaches a certain predetermined level. For that purpose, a gate 53 may include a differential timing device, and an alarm 55 may include a shut-off valve or other output device.

Figure 8:
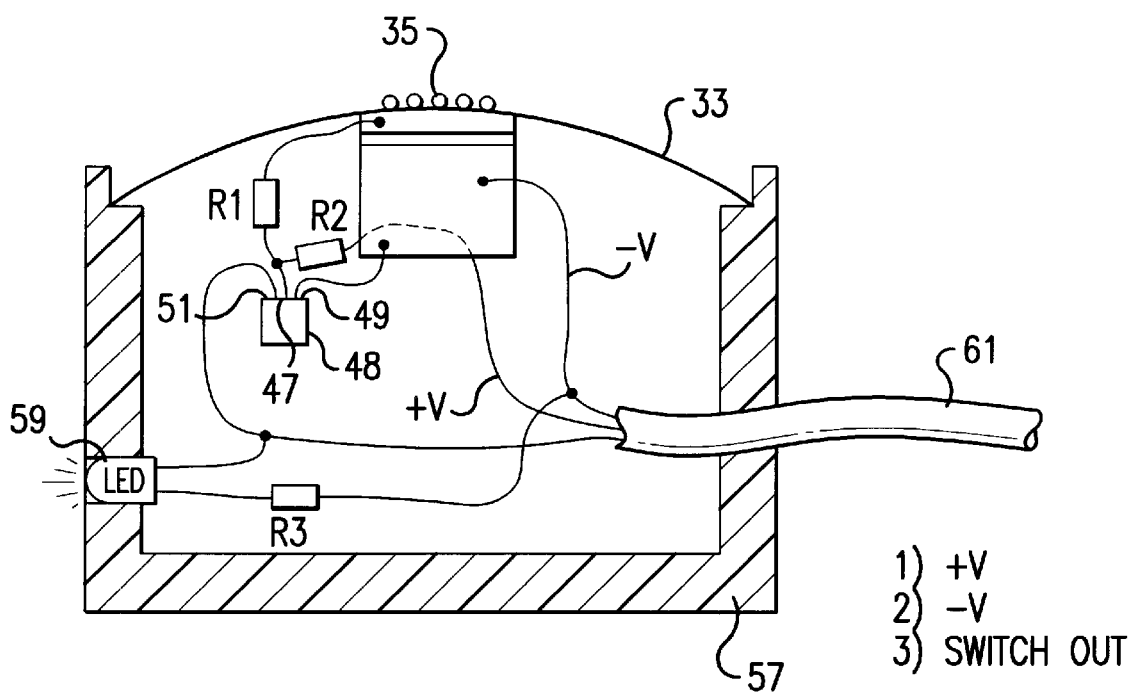
FIG. 8 is schematic view, partly in section, of an assembly of the sensor and diaphragm mounted in a supporting cup partially filled with rigid foam, which may have some thermal conductivity if temperature compensation is required, or may be thermally insulating if no temperature compensation is required, and which also supports a transistor circuit to receive the output signals of the sensor.

In the practice of the invention for purposes such as control of an irrigation system, it will be useful to mount the sensing and switching circuit in a container 57, as shown in FIG. 8 of the drawings. The container may, for instance, be a simple plastic cup that is open at its upper end to receive diaphragm 33, the edge of which may fit into a groove around the inner side of the top edge of container 57. An indicator light 59 may be mounted in the wall of container 57 to give a visual indication of the output signal that is transmitted from container 57 via a cable 61. The indicator light may comprise a light-emitting diode or other inexpensive electric-to-light transducer. A suitable transistor for use in this application is the general-purpose switching transistor type 2N4424.

In the foregoing discussion, the temperature from which tablet 21 departs when switch 39 is closed has been referred to simply as "ambient temperature". The tacit assumption has been that, at the end of each cycle of operation of the sensing and switching circuit, the material of tablet 21 cools off and returns to the same ambient temperature. In that way, a meaningful comparison can be made among the periods of time required for the transistor to become non-conducting. Such a meaningful comparison makes possible the compilation of a "calibration curve" relating the "switch-off time" to the amount of heat-capacity material present on the surface of diaphragm 33. But if the ambient temperature varies with the passage of time, there will be a change in the relationship between "switch-off time" and the amount of heat-capacity material unless a way is found to compensate the operation of the sensing and switching circuit for the change in ambient temperature. Such a way has been found, and will now be described.

We recall that the operation of the invention depends upon one portion of a tablet 21 of PTC material dissipating or transferring more beat to a heat-capacity material than does another portion of the tablet. In the foregoing discussion, the heat transfer occurred from one portion, whereas the other portion was assumed not to transfer heat to the heat-capacity material. The rate of heat transfer is a function of the temperature difference between the heat-capacity material and the heat-transferring portion of the tablet. Therefore, if the ambient temperature rises and carries with it the temperature of the heat-capacity material, the temperature differential between that material and the tablet of PTC material will decrease, and the heat power transferred between them will decrease. The current flowing through the tablet and the series resistors will decrease, thereby causing the bias of the transistor to decrease and cut off the transistor earlier than would otherwise be the case. Thus, the correlation between "switch-off time" and the amount of heat-capacity material would be impaired.

Figure 6:
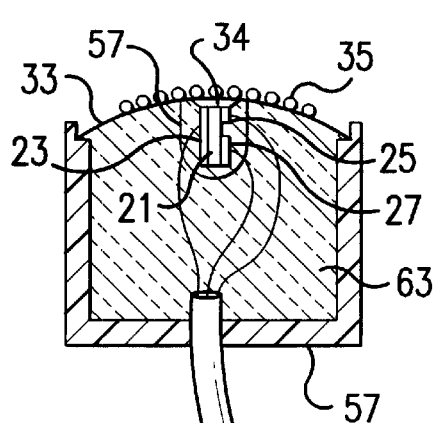
FIG. 6 is a side view, similar to FIG. 3 and depicted partly in section, of a sensor and diaphragm heat sink in accordance with this invention, in which the sensor has been partially enclosed in a rigid foam having some thermal conductivity so that the portion of the sensor remote from the diaphragm heat-sink is loosely coupled thereto in order to achieve temperature compensation of the sensor; and in which the sensor, diaphragm heat sink, and rigid foam are supported by a cup.
Figure 7:
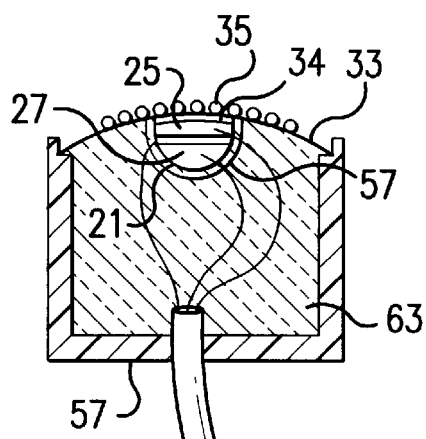
FIG. 7 is a front view, similar to FIG. 4 and depicted partly in section, of a sensor and diaphragm heat sink in accordance with this invention, in which, as in FIG. 6, the sensor has been partially enclosed in a rigid foam having some thermal conductivity, and in which the sensor, diaphragm heat-sink, and rigid foam are supported by a cup.

Now, the way to compensate the operation of the invention for changes in ambient temperature is to maintain "tight" thermal coupling between the diaphragm and the portion of tablet 21 adjacent the diaphragm, while simultaneously providing "loose" thermal coupling between the diaphragm and the portion of tablet 21 remote from it. As illustrated in FIG. 6 and FIG. 7, container 57 can be substantially, filled with a rigid foam 63 having a moderate thermal conductivity and which contacts diaphragm 33, first layer 23, first zone 25, and second zone 27. The foam should be electrically non-conductive, but serves the function of lending mechanical support to tablet 21 in container 57. Foam 63 may comprise a "Room-Temperature-Vulcanization (RTV)" silicone material such as is marketed by the General Electric Company and by Dow Corning Corporation. The Dow Corning product has the type number "732".

In addition to providing foam 63, the temperature compensation is implemented as shown in FIG. 10 by coupling first zone 25 to a voltage divider comprising a third resistor 65 and a fourth resistor 67, while second zone 27 is coupled to another voltage divider comprising a fifth resistor 69 and a sixth resistor 71. The remote ends of both voltage dividers are grounded or connected to sources of steady voltage, preferably negative. The node between third resistor 65 and fourth resistor 67 is connected to a first input terminal 73 of a comparator 75, while the node between fifth resistor 69 and sixth resistor 71 is connected to a second input terminal 77 of comparator 75.

In an earlier paragraph, it was explained that, for the circuit configurations of FIG. 2 through FIG. 5, an increase in ambient temperature will carry with it the temperature of the heat-capacity material interfacing with diaphragm 33, so that the temperature differential between that heat-capacity material and the portion of tablet 21 proximate first zone 25 decreases. Consequently, the heat power transferred between them will decrease, and the current flowing through the tablet and the series resistors will decrease, thereby decreasing the bias of the transistor and tending to cut it off.

In FIG. 10, by contrast, each of the two portions of tablet 21 is connected to a separate voltage divider, and the outputs of those two voltage dividers are fed to respective input terminals of a comparator. The heat power transferred by both portions of the tablet to the heat-capacity material decreases, but at different rates. The heat power transferred by the portion proximate first zone 25 will still decrease at a rate more rapid than the heat power transferred by the portion proximate second zone 27 because the first-named portion is thermally coupled to the heat-capacity material more tightly than the second-named portion. The input voltages fed to the respective input terminals of comparator 75 will move in the same direction, thus achieving some thermal compensation of the sensing circuit. However, the voltage derived from the node between third resistor 65 and fourth resistor 67 and fed to first input terminal 73 of comparator 75 will still prevail over the voltage derived from the node between fifth resistor 69 and sixth resistor 71, and fed to second input terminal 77 of the comparator. Accordingly, the "compensation" does not fully cancel out the useful measure of heat transferred to a heat-capacity material and, thus, provides a useful net signal for amplification by comparator 75 and for delivery to a second transistor switch 79. If that switch is to be protected from signal feedback from its load, an optical isolator 81 or other similar device may be connected in the output circuit of second transistor switch 79. The result of this temperature compensation is to enable the sensing device to detect the presence of, or even measure, heat-capacity material such as water or oil in contact with diaphragm 33 despite changes in ambient temperature.

Earlier paragraphs of this specification have disclosed that the sensing and measuring circuit in accordance with this invention may be operated on a cyclical basis by periodically closing and opening switch 39, through which the circuit is energized. Following each closure of the switch, observations may be made concerning the behavior of the circuit as a function of time. First transistor 48 turns "on" very shortly after closure of the switch but then turns "off" after a period of time which depends upon the amount of heat-capacity material on the surface of diaphragm 33. Thus, the time to "turn-off" is a measure of the amount of heat-capacity material (such as water.)

After first transistor 48 turns off, the circuit returns to a "steady state," which may be interrupted by the opening of switch 39. Then, after switch 39 has been opened, a sufficient period of time should be allowed for tablet 21 to cool back down to ambient temperature. This "cooling-off period" might be ten or twenty minutes if no artificial cooling is employed, but much less if tablet 21 is artificially cooled.

The sensors illustrated in FIG. 6 and FIG. 7 and the sensing-and-measuring circuit illustrated in FIG. 10 provide for the possibility that the ambient temperature, and hence the temperature of tablet 21, may change before switch 39 is re-closed to initiate the next cycle of sensing and measurement. The "temperature compensation" provided by the sensing-and-measuring circuit of FIG. 10 has already been described.

The simplest case or circumstance for the operation of the respective electronic circuits of either FIG. 5 or FIG. 10 is the case in which it is sufficient to determine whether a heat-capacity material, such as water, is or is not present on diaphragm 33, which in turn is in thermal contact with the first zone of the second ohmic layer of tablet 21. In the time plot of FIG. 9B, that is the significance of the respective subscripts "WET" and "DRY" on the representations of the currents through first transistor 48. On the other hand, those subscripts could be taken to mean "more wet" and "less wet" if the amount or concentration of moisture is to be measured rather than merely detected. A calibration curve relating concentration of moisture to the difference between the two times indicated in FIG. 9B then gives the concentration of moisture. This could be, for instance, the amount of water suspended in a sample of earth under a golf green undergoing irrigation.

Figure 11:
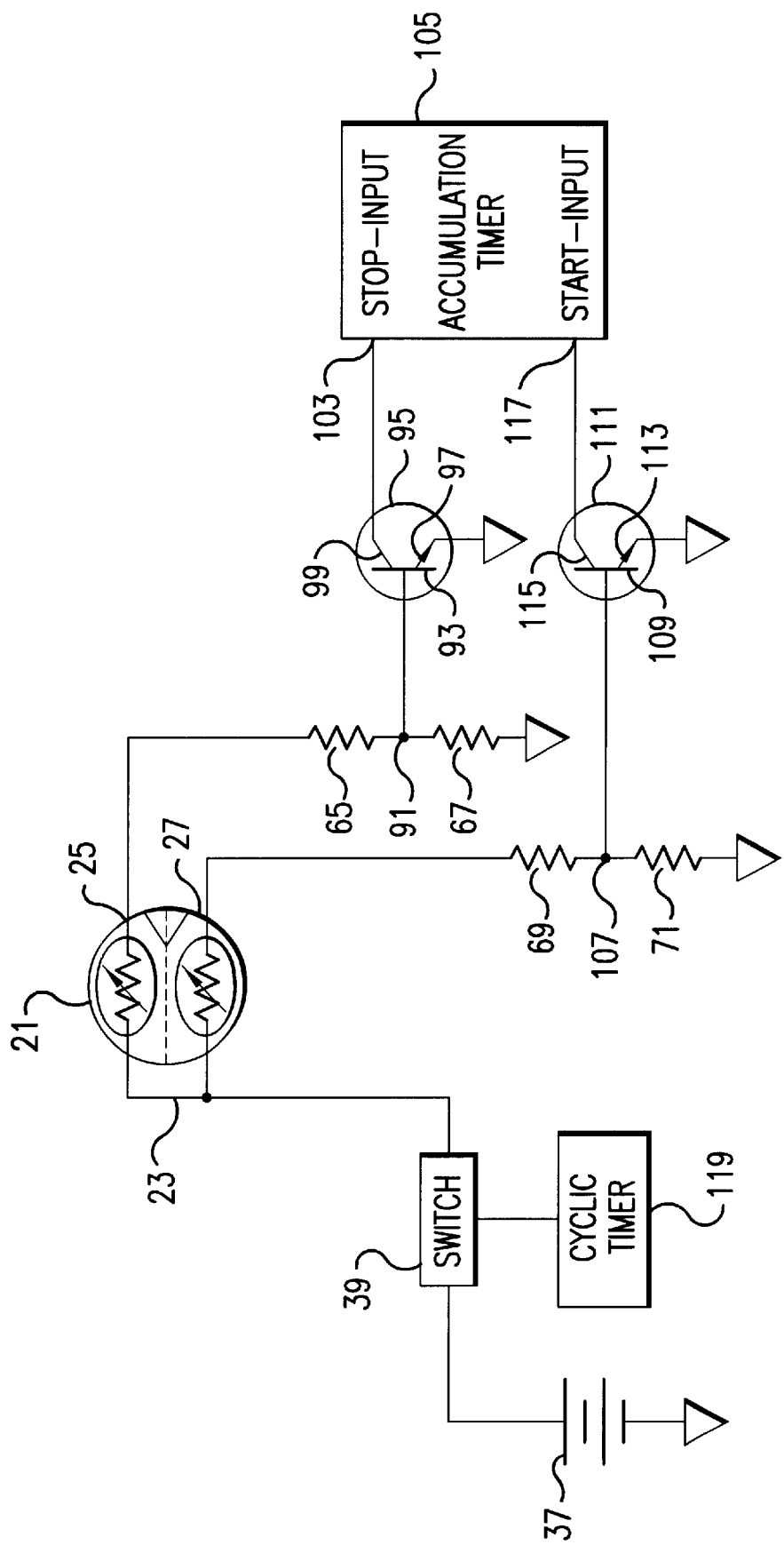
FIG. 11 is a schematic representation of a sensing, switching, and measuring circuit in accordance with this invention in which signals from the first and second zones of the second ohmic layer of the sensor are fed to respective first and second transistors, which provide switching wave forms to an accumulation timer for measuring time disparity between switching events when the sensor is with and without heat sinking, e.g., by moisture on the surface of the diaphragm.

A more sophisticated sensing, switching, and measuring circuit is illustrated in FIG. 11 of the drawings. In FIG. 11, as in FIG. 10, tablet 21 of PTC material is represented schematically as a pair of variable resistors connected in parallel but feeding output signals to separate respective pairs of resistors which act as voltage dividers. In both FIG. 10 and FIG. 11, as well as in FIG. 5, the conductor having the reference numeral 23 represents first layer 23 of ohmic material which, for present purposes, may be regarded as being adhered to one side of tablet 21. (As will be explained later in this specification, first layer 23 of ohmic material need not necessarily be on the side of tablet 21 opposite to first zone 25 and second zone 27 of ohmic material.)

In FIG. 11, as in FIG. 10, third resistor 65 and fourth resistor 67 together constitute the first voltage divider, while fifth resistor 69 and sixth resistor 71 together constitute the second voltage divider. A second node 91, between third resistor 65 and fourth resistor 67, is connected to a base 93 of a second transistor 95 having also an emitter 97 and a collector 99. Second transistor 95 may be an NPN transistor in which emitter 97 is grounded. Another type of current-sensitive switching device may be employed. But, if an NPN transistor is selected for this purpose, a Type 2N4424 general-purpose transistor will suffice. Collector 99 may be connected to a "stop" input terminal 103 of an accumulation timer 105.

A third node 107, between fifth resistor 69 and sixth resistor 71, is connected to a base 109 of a third transistor 111 having also an emitter 113 and a collector 115. Collector 115 of third transistor 111 may be connected to a "start" input terminal 117 of accumulation timer 105, which may be an integrated circuit such as the Philips N74 F 161AN four-bit binary counter.

Returning to tablet 21, first layer 23 of ohmic material is connected through switch 39 to source 37 of positive potential "+V." Switch 39 is controlled by a cyclic timer 119, (such as Philips 74 HCT5555N programmable delay timer), which may cause switch 39 to be closed and opened periodically. Once again, tablet 21 of PTC material, which is represented schematically in FIG. 10 and FIG. 11, could take the physical form shown in the side view of FIG. 6 and the front view of FIG. 7. First zone 25 of ohmic material is electrically separated from second zone 27 of ohmic material by removing a narrow strip of ohmic material between them. Nevertheless, the two zones do have some minor electrical communication through the body of tablet 21, to which they are both attached. As has been mentioned, reasonable compensation can be achieved for changes in ambient temperature by loosely coupling to diaphragm 33, and its burden of moisture (the heat sink), the portion of tablet 21 proximate second zone 27 of ohmic material. This loose thermal coupling is accomplished through the rigid foam 63, which may also be used to support tablet 21 in container 57 and in contact with diaphragm 33. It will be understood that a membrane or other thin but strong structure may be substituted for diaphragm 33. Close physical and thermal contact may be maintained between the portion of tablet 21 proximate first zone 25 of ohmic material and diaphragm 33, or a membrane or equivalent structure, by means of a layer of thermal epoxy 34 (FIG. 6 and FIG. 7). Accordingly, the portion of tablet 21 proximate first zone 25 of ohmic material continues to be thermally tightly coupled to the heat sink. In this way, the heating time of the portion of tablet 21 proximate second zone 27 is somewhat controlled by the ambient temperature, whereas the heating time of the portion of tablet 21 proximate first zone 25 is still primarily controlled by the heat-sink comprising diaphragm 33 and its burden of moisture or other substance to be sensed and measured.

For the purpose of explanation of the operation of the circuit of FIG. 11 as illustrated in the time plots of FIG. 12 and FIG. 13, let us assume that water drops 35 may either appear like raindrops on the surface of diaphragm 33 or may take the form of moisture suspended in earth as if the sensor were "buried" in the earth under a golf green or an irrigated field. When switch 39 is closed, thereby applying a positive potential "+V" to first layer 23 of ohmic material, electric current will flow through tablet 21, which is then in its low-resistance state. Both portions of tablet 21 will begin to heat up in accordance with the familiar expression $I^2R$ governing the generation of heat. Each incremental portion of tablet 21 has its own "$I^2R$" determined by the resistivity and current density at that point in the PTC material. Each increment of material finds its own way from left to right and then up the steep slope of the plot of FIG. 1. Because of the heat transferred to the heat sink through diaphragm 33, the portion of tablet 21 proximate first zone 25 of ohmic material will reach the Curie point and attain its high-resistance mode later than does the portion of tablet 21 proximate second zone 27 of ohmic material. When the respective portions of tablet 21 reach the Curie point, the respective currents through them and through first zone 25 and second zone 27 will decrease abruptly—at different times.

It is noteworthy from FIG. 11 that the current through the portion of tablet 21 proximate second zone 27 is determined primarily by the voltage "+V" from source 37 and by the respective resistances of that particular portion and of fifth resistor 69 and sixth resistor 71. The latter should be low in magnitude so as not to impede unduly the initial rush of current through the portion of tablet 21 proximate second zone 27. Similarly, third resistor 65 and fourth resistor 67 should be low in magnitude so as not to impede unduly the initial rush of current through the portion of tablet 21 proximate first zone 25. The portion of tablet 21 proximate second zone 27 will heat up quickly, and the current through it will decrease until it finds a stable operating point on the steep slope of the plot of FIG. 1. The operating point will be determined by the balance between $I^2R$ heat power supplied by source 37 and the rate of heat dissipation to the environment of that portion of tablet 21.

The portion of tablet 21 proximate first zone 25 will heat up more slowly because of the drain of heat power into the heat sink comprising diaphragm 33 and whatever moisture, earth, or other material may be in contact with it. But after some time, this portion, too, will probably reach the Curie point and begin a sharp increase in resistance. The current through it will then decrease until the $I^2R$ heat power supplied by source 37 comes into stable equilibrium with the rate of heat dissipation to the heat sink. The voltage "+V" should be chosen so that the point of stable equilibrium is well up on the steep slope of the plot of FIG. 1. For typical applications, a potential of 24 volts has been used. But this suggestion is not to be taken in a limiting sense. Moreover, it will be understood that the heat sink in thermal communication with the portion of tablet 21 proximate first zone 25 may take a form other than a diaphragm burdened with drops of water. It could, for instance, be a body of resin undergoing melting, whose temperature is to be sensed.

Second node 91, between third resistor 65 and fourth resistor 67, is connected to base 93 of second transistor 95. Emitter 97 of second transistor 95 may be grounded, while collector 99 may be connected to "stop" input terminal 103 of accumulation timer 105. Third node 107, between fifth resistor 69 and sixth resistor 71, is connected to base 109 of third transistor 111. Emitter 113 of third transistor 111 may be grounded, while collector 115 of third transistor 111 may be connected to "start" input terminal 117 of accumulation timer 105.

When switch 39 is closed and voltage "+V" from source 37 is applied to first layer 23 of ohmic material of tablet 21, there will be surge of current through both the portion of tablet 21 proximate first zone 25 and the portion of tablet 21 proximate second zone 27. The voltages at both second node 91 and third node 107 will be well in excess of 0.7 volt. Consequently, both second transistor 95 and third transistor 111 will turn on, and currents will flow through their respective collectors. However, those similar currents will not initiate timing by accumulation timer 105. The sharp rise in respective voltages is illustrated in FIG. 12A and FIG. 12B.

The $I^2R$ heating causes the portion of tablet 21 proximate second zone 27 to reach and exceed its Curie point, whereupon the resistance of that portion increases sharply, and the current through it falls, as shown in FIG. 12B for the "Second Zone." Accordingly, the voltage at third node 107 falls below 0.7 volt, and third transistor 111 turns off. This event occurs whether or not diaphragm 33, in thermal contact with the "First Zone" of tablet 21, is loaded with heat-capacity material such as water. When third transistor 111 turns off, the signal transmitted to "start" input terminal 117 causes accumulation timer 105 to start timing.

The $I^2R$ heating of the portion of tablet 21 proximate first zone 25 ("First Zone" in FIG. 12A) occurs more slowly because of the heat dissipated or transmitted to the heat sink comprising diaphragm 33 and the water or other material, if any, which resides on the side of the diaphragm 33 remote from tablet 21. However, unless the heat-sinking effect is very great, the First Zone does eventually reach and surpass its Curie point, whereupon its resistance increases sharply, and the current through it falls. As shown in FIG. 12A, the voltage at second node 91 falls below 0.7 volt, and second transistor 95 turns off. Collector 99 then transmits a signal to "stop" input terminal 103 which causes accumulation timer 105 to stop timing.

When second transistor 95 turns off and accumulation timer 105 stops timing, the resultant time indicated by accumulation timer 105 is essentially the difference between the respective times required by First Zone and Second Zone to reach and surpass the Curie temperature. This time difference is substantially proportional to the heat-sinking effect. To the degree that the heat capacity of diaphragm 33 can be disregarded, this time difference is a measure of the quantity of water or other substance present on the surface of diaphragm 33.

For the sake of explanation, let us refer to a "wet diaphragm" and a "dry diaphragm." As illustrated in FIG. 12B, the plot of voltage at third node 107 (coupled to the Second Zone of tablet 21) is the same whether diaphragm 33 is wet or dry. However, as shown in FIG. 12A, the plot of voltage at second node 91 (coupled to the First Zone of tablet 21) depends in an important way on whether diaphragm 33 is dry or wet—and if wet, then how wet. The wetter the diaphragm, the longer is the delay before the voltage at the second node 91 falls below 0.7 volt, thus turning off second transistor 95 and causing collector 99 to transmit a signal to "stop" input terminal 103. In the lower part of FIG. 12B, the time between the "wet stop" and the "dry stop" is the measure of the quantity of water or other substance present on the surface of diaphragm 33. In each case, a "calibration curve" can be drawn, relating the time difference to the amount of "heat-sink material," such as water.

FIG. 12C depicts, in a fashion correlated in time to the plots of FIG. 12A and FIG. 12B, the "gating" action of cyclic timer 119 in controlling the energization of first layer 23 of ohmic material from source 37 of positive voltage "+V". Cyclic timer 119 may initiate another cycle of energization, sensing, and time measurement (and hence measurement of heat-sink material) after any desired interval of time, from minutes to days. The tacit assumption has been made that the ambient temperature remains substantially unchanged while the above-described measurements are recorded.

It may be helpful to give a specific example of particular values of components, currents, and voltages that would be satisfactory in the practice of the inventive embodiment illustrated in FIG. 11. These values are exemplary only, and are not to be taken in a limiting sense.

The resistance of a typical tablet 21 at room temperature is approximately 50 ohms. After part of the tablet is removed to form a disk, which can conform to the contour of diaphragm 33, as shown in FIG. 4, FIG. 6, and FIG. 7, the resistance of the remainder is about 80 ohms. When the second layer of ohmic material has been scored or milled to separate it into a first zone 25 and a second zone 27, the resistances of the respective portions of tablet 21 proximate those zones are each in the neighborhood of 160 ohms. (In FIG. 12A and FIG. 12B, those respective portions are referred to as "First Zone" and "Second Zone.")

In order that most of the power from source 37 may be delivered to, and consumed by, tablet 21, third resistor 65, fourth resistor 67, fifth resistor 69, and sixth resistor 71 are set low—of the order of 15 ohms each. If a value of 24 volts is chosen for source 37, closure of switch 39 causes a current of about 0.126 ampere to flow through each of first zone 25 and second zone 27 of ohmic material, producing a potential of approximately 1.89 volts at second node 91 and third node 107. The value of this potential is approximate because some current is diverted at those nodes to produce forward bias of second transistor 95 and third transistor 111 respectively.

When the temperature of the Second Zone of tablet 21 surpasses the temperature of the Curie point, and the resistance of that zone reaches a value of approximately 500 ohms, the voltage at third node 107 falls below 0.7 volt, causing third transistor 111 to turn off and send a signal to "start" input terminal 117, thereby initiating the timing action of accumulation timer 105. The timer continues to run until the temperature of the First Zone of tablet 21 also surpasses the temperature of the Curie point and the resistance of that zone also reaches a value of approximately 500 ohms. At that time, the voltage at second node 91 falls below 0.7 volt, thereby causing second transistor 95 to turn off and send a signal to "stop" input terminal 103. The timing action of accumulation timer 105 then stops, producing a reading, which is a measure of the amount of "heat-sink material," such as water.

As has been explained in the foregoing discussion of FIG. 6 and FIG. 7, tablet 21 may be supported within container 57 by a rigid foam 63 having a moderate thermal conductivity and which contacts diaphragm 33, first layer 23 of ohmic material, and first zone 25 and second zone 27 of the second layer of ohmic material. It will be understood that another material of moderate thermal conductivity may be substituted for the foam, but the foam is relatively easy to form in place around the tablet and its electrical leads.

If the sensing and measuring circuit is left for an extended period of time without being energized from source 37, both the First Zone and the Second Zone of tablet 21 will stabilize at a temperature approximating that of whatever heat-sink material may be in thermal contact with diaphragm 33. Rigid foam 63, or its equivalent material, will likewise tend to assume the temperature of the heat-sink material (e.g. water.) Then, when switch 39 is closed and energy from source 37 is applied to the heat-up of the First Zone and the Second Zone of tablet 21, some of that energy will flow from the Second Zone into rigid foam 63 just as energy flows from the First Zone into diaphragm 33 and the heat-sink material. In fact, heat energy will also flow from the First Zone into rigid foam 63, which is assumed to start from "ambient temperature." Thus, since the rate of heat flow is dependent upon the temperature gradient, the "heat-up rate" of both the First Zone and the Second Zone of tablet 21 will be dependent upon the ambient temperature, and "temperature compensation" will be accomplished.

A complete understanding of the temperature-compensation feature of this invention may be acquired by means of a careful study of FIG. 13 of the drawings. In that figure, the format is similar to FIG. 12, but it is plotted in such a way as to show the effects of a change in ambient temperature. The assumption is made that the temperature of tablet 21 and rigid foam 63 follows an increasing ambient temperature, but that the degree of "wetness" of diaphragm 33 remains constant while the measurement is made, and between measurements.

In FIG. 13B, reference should first be made to the plot labeled "COOL WET." In that plot, the voltage at third node 107, having risen sharply following the closure of switch 39, falls as the Second Zone of tablet 21 heats up. This heat-up takes place despite the dissipation of some heat by the Second Zone to rigid foam 63 at ambient temperature. When the heat-up raises the resistance of the Second Zone to approximately 500 ohms, the voltage at third node 107 will have fallen to 0.7 volt, causing third transistor 111 to turn off, thereby signaling accumulation timer 105 to start timing.

Now, if the ambient temperature and the temperature of rigid foam 63 are increased, the behavior of the circuit-changes to that of the plot labeled "WARM WET." The Second Zone of tablet 21 heats up more rapidly because it is dissipating less heat to rigid foam 63. Consequently, the voltage at third node 107 falls more rapidly after its initial sharp rise. Accordingly, third transistor 111 is turned off sooner, sending an earlier signal to accumulation timer 105 to start timing. In FIG. 13B, the time of the "WARM START" is indicated by a full line, whereas the time of the "COOL START" is indicated by a dash line.

Turning from the behavior of the Second Zone, as illustrated in FIG. 13B, to the behavior of the First Zone, as illustrated in FIG. 13A, we see that a similar acceleration of the "STOP" time occurs when the temperature of foam 63 around the First Zone of tablet 21 changes from "COOL" to "WARM." The voltage at second node 91 rises to a peak in the "WARM WET" plot which is similar to the peak of the "COOL WET" plot, but the "WARM WET" plot thereupon falls more sharply than does the "COOL WET" plot because the First Zone of tablet 21 dissipates less heat to comparatively warm rigid foam 63 than it did to comparatively cool rigid foam 63. Accordingly, second transistor 95 turns off sooner in the "WARM WET" plot than in the "COOL WET" plot, and accumulation timer 105 is caused to stop timing sooner. Again, FIG. 13C shows the "WARM START" and the "WARM STOP" times in full lines, whereas the "COOL START" and "COOL STOP" times are indicated by dash lines. Most significantly, the amount of accumulated time indicated by the full lines is substantially the same as the amount of time indicated by the dash lines. This fact demonstrates the effectiveness of the compensation for change in ambient temperature.

For the sake of explanation of the operation of the circuit, the values of the third through sixth resistors 65 through 71 have been assumed to be equal. However, it will be understood that the value of fourth resistor 67 could be made higher than that of third resistor 65 in order to delay the turn-off of second transistor 95, thereby delaying the end of the operation of accumulation timer 105. Or the relative values of fourth resistor 67 and sixth resistor 71 could be adjusted to overcome the effect of slight differences between the respective thermal couplings of the First Zone and the Second Zone with the adjacent rigid foam 63.

Figure 14:
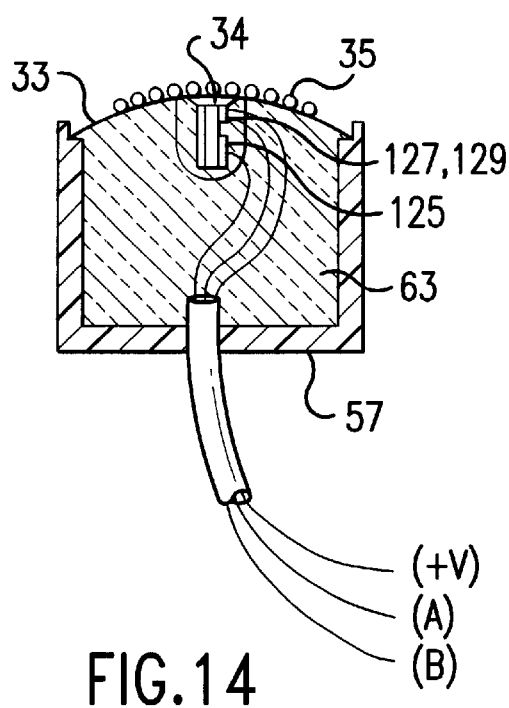
FIG. 14 is a side view, similar to FIG. 6 and depicted partly in section, of a sensor and diaphragm heat sink in accordance with this invention in which the first zone of the second ohmic layer of the sensor is divided into two sub-zones, one of which may be substantially without heat-sinking.
Figure 15:
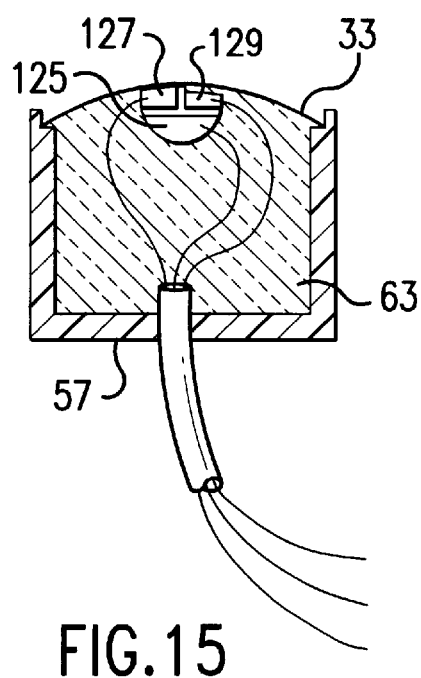
FIG. 15 is a front view, similar to FIG. 7 and depicted partly in section, of a sensor and diaphragm heat sink as illustrated in FIG. 14 and showing one mode of division of the first zone of the second ohmic layer into two subzones.
Figure 16:
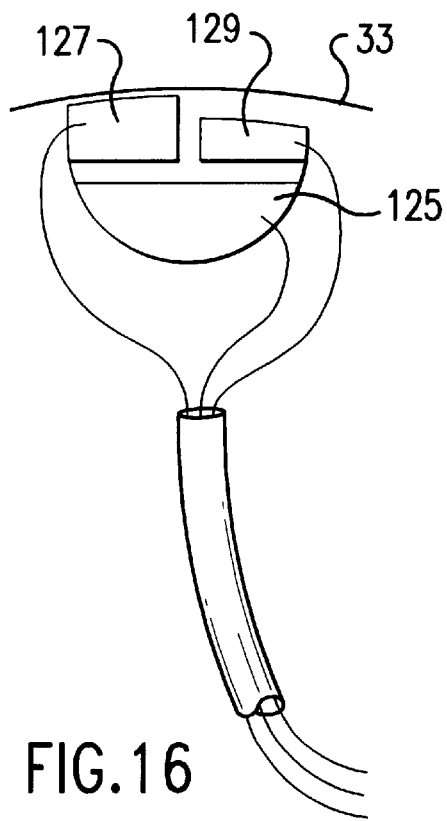
FIG. 16 is an enlarged front view, depicted partly in section, showing a mode of division of the first zone of the second ohmic layer into two sub-zones.

Also for the sake of explanation of the operation of the circuit, it has been assumed that first layer 23 of ohmic material is on one side of tablet 21 of PTC material and that, on another side of tablet 21 are positioned first zone 25 and second zone 27 of ohmic material. Actually, all three of those components may be positioned on the same side of tablet 21, as shown in FIG. 14, FIG. 15, and FIG. 16 of the drawings. In those figures, an ohmic base zone 125 is located on a surface of tablet 21 remote from diaphragm 33, while a first sub-zone 127 and a second sub-zone 129 of ohmic material are located on the surface of tablet 21 between base zone 125 and diaphragm 33. First sub-zone 127 is in thermal contact with diaphragm 33, but second sub-zone 129 is not. Each of base zone 125 and first sub-zone 127 and second sub-zone 129 is in electrical contact with tablet 21, but not directly with one another. On the same surface of tablet 21, the ohmic material separating base zone 125, first sub-zone 127, and second sub-zone 129 has been removed by scoring or milling or otherwise. But all of those elements are nevertheless in indirect electrical communication through the PTC material of tablet 21.

In FIG. 15 and FIG. 16, it is apparent that first sub-zone 127 is analogous to first zone 25 of ohmic material, which has been frequently mentioned in earlier discussions of FIG. 3 and FIG. 4. Further, second sub-zone 129 is analogous to second zone 27 of ohmic material, which has likewise been mentioned in earlier paragraphs, but is positioned on the same side of tablet 21 as base zone 125. In some applications, this mode of array may be more useful than the mode of array previously discussed.

Although full disclosure and discussion of the various aspects of the apparatus and operation thereof in accordance with my invention have been presented in the foregoing paragraphs, it is possible that certain variations thereof can be made in the future without departing from my invention. Accordingly, the scope of my invention is defined in the following claims, which cover the elements of my invention and equivalents thereof.

I claim:

1. In combination,
   (a) a tablet of positive-temperature-coefficient material having a continuously-electrically-conductive first surface and a second surface which is discontinuously electrically conductive so as to separate said second surface into at least a first conductive zone and a second conductive zone which are not in electrical contact with each other except through said positive-temperature-coefficient material,
   (b) means for electrically energizing said first surface,
   (c) means for connecting said second conductive zone to a steady level of electrical potential,
   (d) resistive means for connecting said first conductive zone to a steady level of electrical potential, said resistive means comprising a first resistive segment and a second resistive segment, joined in series through a node,
   (e) switching means connected to said node, and
   (f) means for thermally coupling said first conductive zone of said second surface, and the portion of said tablet adjacent thereto, to a heat receptor.

2. The combination in accordance with claim 1 in which said switching means is a transistor.

3. The combination in accordance with claim 1 in which said switching means is an NPN transistor having its base connected to said node between said first resistive segment and said second resistive segment.

4. The combination in accordance with claim 2, further including output means connected to said transistor.

5. The combination in accordance with claim 3, further including output means connected to the collector of said NPN transistor.

6. The combination in accordance with claim 1 in which said thermal coupling means is a diaphragm in contact with said portion of said tablet adjacent said first conductive zone of said second surface.

7. The combination in accordance with claim 6 in which said diaphragm is bonded to said portion of said tablet adjacent said first conductive zone of said second surface.

8. The combination in accordance with claim 1 in which said means for electrically energizing said first surface includes a switch.

9. The combination in accordance with claim 8, further including a timer for periodically actuating said switch.

10. The combination in accordance with claim 4 in which said output means includes a NOT gate.

11. The combination in accordance with claim 4 in which said output means includes an alarm.

12. The combination in accordance with claim 10, further including an alarm connected to said NOT gate.

13. The combination in accordance with claim 1, further including a supporting matrix of plastic foam.

14. The combination in accordance with claim 13 in which said plastic foam is characterized by substantial thermal conductivity.

15. The combination in accordance with claim 13, further including a receptacle surrounding and retaining said plastic foam.

16. In combination,
   (a) a body of positive-temperature-coefficient material having a continuously-electrically-conductive first surface and a second surface which is discontinuously electrically conductive so as to separate said second surface into at least a first conductive zone and a second conductive zone which are not in electrical contact with each other except through said positive-temperature-coefficient material,
   (b) means for electrically energizing said first surface,
   (c) first and second resistive means for connecting said first conductive zone to a steady level of electrical potential, said first and second resistive means being deployed in series and having a first node between them,
   (d) third and fourth resistive means for connecting said second conductive zone to a steady level of electrical potential, said third and fourth resistive means being deployed in series and having a second node between them,
   (e) a comparator having first and second input terminals connected respectively to said first node and said second node and having also an output terminal, and
   (f) switching means having an input terminal connected to said output terminal of said comparator.

17. The combination in accordance with claim 16 in which said switching means is a transistor.

18. The combination in accordance with claim 17, further including an optical isolator connected between the collector and emitter of said transistor.

19. The combination in accordance with claim 16 in which said means for electrically energizing said first surface includes means for periodically applying a predetermined electrical potential.

20. The combination in accordance with claim 19 in which said means for periodically applying a predetermined electrical potential includes a clock and a switch, said clock controlling the operation of said switch, and said switch being connected to said first surface of said positive-temperature-coefficient material.

21. In combination,
   (a) a body of positive-temperature-coefficient material having at least three electrically-conductive surfaces which are not in electrical communication with one another except through said positive-temperature-coefficient material, (b) means for electrically energizing a first one of said conductive surfaces, (c) first and second resistive means for connecting a second one of said conductive surfaces to a steady level of electrical potential, said first and second resistive means being deployed in series and having a first node between them, (d) third and fourth resistive means for connecting a third one of said conductive surfaces to a steady level of electrical potential, said third and fourth resistive means being deployed in series and having a second node between them, (e) a first transistor having its base connected to said first node and its emitter connected to a steady level of electrical potential, (f) a second transistor having its base connected to said second node and its emitter connected to a steady level of electrical potential, and (g) an accumulation timer having its stop-input terminal connected to the collector of said first transistor and its start-input terminal connected to the collector of said second transistor.

22. The combination in accordance with claim 21 in which said means for electrically energizing said first one of said conductive surfaces includes a switch.

23. The combination in accordance with claim 22, further including a cyclic timer for periodically actuating said switch.

\* \* \* \* \*